United States Patent [19]

Brandelik

[11] Patent Number: 5,073,756
[45] Date of Patent: Dec. 17, 1991

[54] METHOD AND APPARATUS FOR MEASURING THE VOLUMETRIC WATER CONTENT OF MINERAL AND/OR ORGANIC MIXTURES

[75] Inventor: Alexander Brandelik, Karlsruhe, Fed. Rep. of Germany

[73] Assignee: Kernforschungszentrum Karlsruhe GmbH, Karlsruhe, Fed. Rep. of Germany

[21] Appl. No.: 543,133

[22] Filed: Jun. 25, 1990

[30] Foreign Application Priority Data

Jun. 24, 1989 [DE] Fed. Rep. of Germany ....... 3920787

[51] Int. Cl.⁵ .................... G01N 22/04; G01R 27/06
[52] U.S. Cl. .................................. 324/643; 324/646; 324/637; 324/632
[58] Field of Search ............. 324/640, 643, 646, 664, 324/670, 687, 689, 690, 632, 637, 639, 642

[56] References Cited

U.S. PATENT DOCUMENTS

| | | | |
|---|---|---|---|
| 3,079,552 | 2/1963 | Walker | 324/643 X |
| 3,581,197 | 5/1971 | Morey, Jr. | 324/690 |
| 4,044,607 | 8/1977 | Deal | 324/689 X |
| 4,155,035 | 5/1979 | Fitzky | 324/585 C |
| 4,206,399 | 6/1980 | Fitzky et al. | 324/643 |
| 4,278,934 | 7/1981 | Ihara et al. | 324/690 |
| 4,399,404 | 8/1983 | Resh | 324/689 |
| 4,850,386 | 7/1989 | Bireley | 324/689 X |

FOREIGN PATENT DOCUMENTS

| | | |
|---|---|---|
| 566551 | 7/1975 | Fed. Rep. of Germany. |
| 2552954 | 6/1977 | Fed. Rep. of Germany. |
| 2719039 | 8/1978 | Fed. Rep. of Germany. |
| 3402708 | 8/1985 | Fed. Rep. of Germany. |

OTHER PUBLICATIONS

"Neuere Entwicklungen von Mikrowellen-Feuchtemessgeräten für Labor und Betrieb" by H. G. Fitzky, G-I-T, Oct. 1977, pp. 1062-1070.

Primary Examiner—Jack B. Harvey
Attorney, Agent, or Firm—Spencer & Frank

[57] ABSTRACT

A method and an apparatus for determining the volumetric water content of a mineral and/or organic mixture with dielectric measurements. The apparatus includes a probe body having a hollow cylinder formed of an insulating material with an annular cutting edge at a lower end. Electrodes and a temperature sensor are carried by the probe body. A bottom plate may be disposed adjacent to the lower end of the cylinder so that the cylinder and the plate define a cavity for receiving a liquid coolant. A removable cover is provided for closing the cavity to prevent rain water from entering. The method includes introducing the probe in the mixture, charging the electrodes with a high frequency electromagnetic wave so as to generate an HF field in a region of the electrodes and reflect a wave from the electrodes, measuring a complex reflection factor of the reflected wave at a temperature $T_1$ of the mixture, cooling the surrounding mixture to a temperature $T_2$ so as to freeze the water therein by closing the bottom the probe with the plate and inserting the coolant into the cavity, measuring the reflection factor with the surrounding mixture at the temperature $T_2$, determining the dielectric constant for the mixture at the temperatures $T_1$ and $T_2$ from the measured reflection factors with the aid of an invariable probe-specific calibration curve, and calculating the volumetric water content of the mixture from the two determined dielectric constants and the known dielectric constants of water and ice.

17 Claims, 1 Drawing Sheet

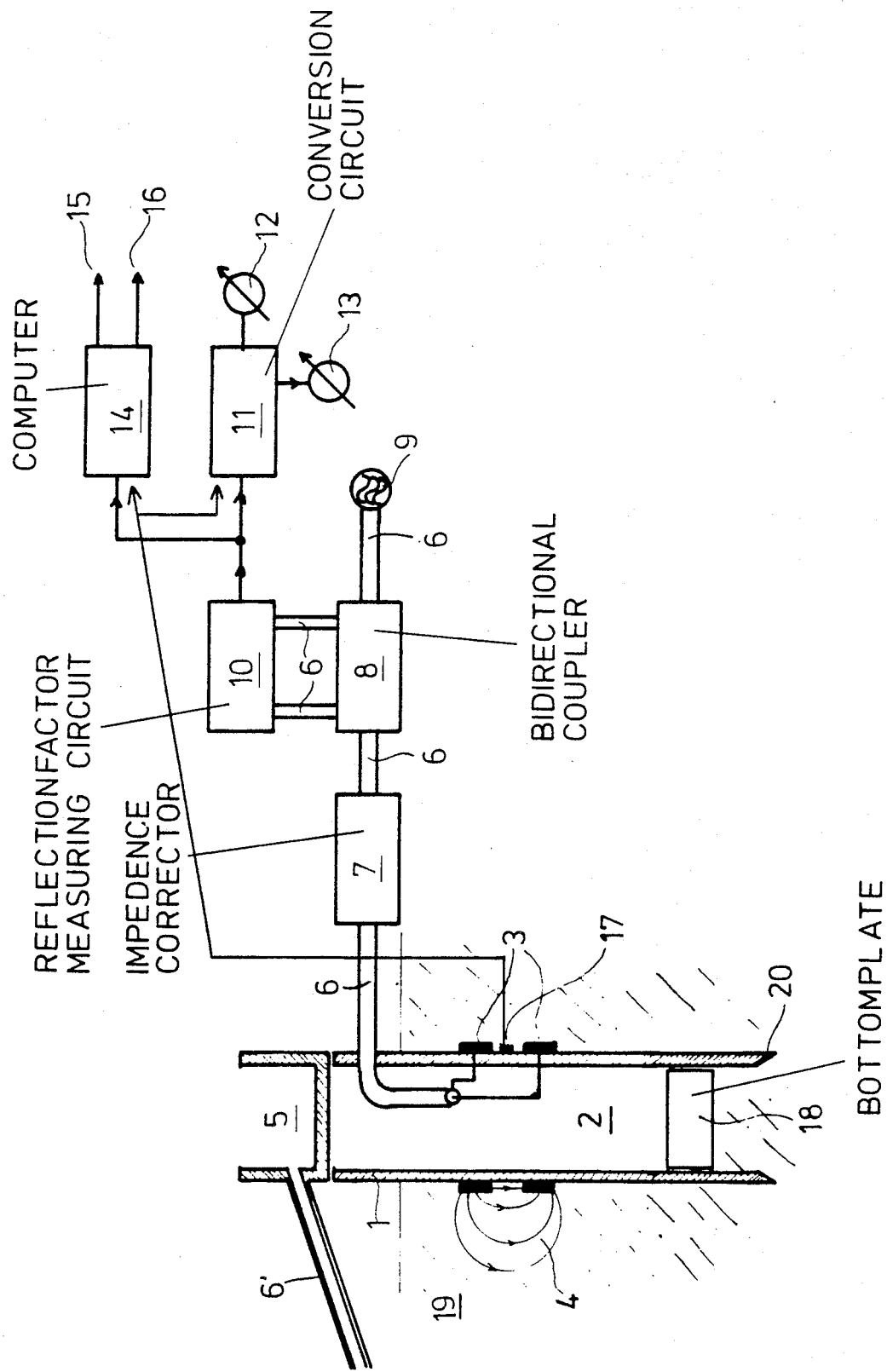

METHOD AND APPARATUS FOR MEASURING THE VOLUMETRIC WATER CONTENT OF MINERAL AND/OR ORGANIC MIXTURES

REFERENCE TO RELATED APPLICATIONS

This application claims the priority of Federal Republic of Germany application Serial No. P 39 20 787.0 filed June 24th, 1989, which is incorporated herein by reference.

BACKGROUND OF THE INVENTION

The present invention relates to a method for measuring the volumetric water content of mineral and/or organic mixtures by means of dielectric measurements with the aid of a probe including at least two measuring electrodes. The invention further relates to an apparatus for measuring the volumetric water content of mineral and/or organic mixtures by means of dielectric measurements with the aid of a probe having a probe body carrying at least one electrode arrangement in the form of a two-conductor or three-conductor system.

Meteorological models require a precise knowledge of the water contents in the ground soil since, due to the great heat retention capacity of water compared to air, the exchange of energy between the ground and the atmosphere is transacted primarily by evaporation and condensation of water. In hydrology, a precise knowledge of the water content of the ground forms the basis of all planning. In agriculture, optimum watering is impossible without a precise determination of water content of the soil. Insufficient watering leads to damage of the plants while too extensive watering results in a leaching out of nutrients. In drying processes, a precise knowledge of water content produces advantages of economy since drying processes are very energy intensive.

Generally, determinations of moisture content of soil and other mineral and/or organic mixtures are made using probes to determine their dielectric constant. In DE 3,402,708.A1 and in the operating instructions for the BF 610 instrument produced by Philipp Schenk GmbH Wien & Co. KG, Jedleseer Strasse 59, A-1210 Vienna, Austria, two devices are described for measuring soil moisture. Each of these devices is pushed into the ground in order to make the measurements. Pushing such a device into the soil changes the density of the soil. Because the compression is effected concomitantly with a reduction in the percentage of air in the soil, the water which is present becomes concentrated in a smaller volume. That causes the measurement to be incorrect. Moreover, the change in density remains in effect for a very long time, and the measurement is no longer representative of an uninterferred-with volume.

From the measured values of dielectric constant, the moisture content of the soil can be determined only by way of a calibration curve which can only be prepared in the laboratory using a complicated procedure. Moreover, the determination must be made separately for each type of soil. For this purpose, a representative soil sample of a particular type is drawn and dried completely. After adding different defined amounts of water to the sample, measurements on the sample are made and the results used to form the calibration curve.

Ground soil is an important example of mixtures containing three or more components, to which the invention is applicable. A fraction of the volume of a soil mixture to be measured is the dry soil B; in addition, a fraction W is water and a fraction L is air so that:

$$L + W + B = 1.$$

The dielectric constant of this mixture, $\epsilon_{g1}$, is equal to the weighted sum of the dielectric constants of the components of the mixture. Thus, $$\epsilon_{g1} = B \cdot \epsilon_B + W \cdot \epsilon_W + L \cdot \epsilon_L$$

wherein $\epsilon_B$ is the dielectric constant of the dry soil, $\epsilon_W$ is the dielectric constant of water, and $\epsilon_L$ is the dielectric constant of air. Generally, B, $\epsilon_B$ and W of this equation are unknown. An error in the results obtained with the prior art methods resides in the fact that $B \cdot \epsilon_B$ and $L \cdot \epsilon_L$ are neglected. The smaller the water content, the greater is this error. Many probe manufacturers therefore recommend calibration of the probe for the respective mixtures according to the water content. Such a calibration requires that several very precise samples be taken. Moreover, the measurements involved are difficult to carry out accurately since, as noted above, they are subject to error if the samples are compressed as they are taken. Further, the measurements require the use of time consuming and energy intensive heating processes.

If the area of the upper surface of the probe (the probe cover) is approximately the same as the area of a vertical projection of the volume of the soil mixture to be measured, rain water flowing off from the cover falsifies the measuring result. The concentration of rain water in the vicinity of the probe also causes difficulty in performing the measurements because the outflowing water washes out channels between the soil and the probe wall.

SUMMARY OF THE INVENTION

An object of the present invention is to provide a method and an apparatus for determining the volumetric water content of mineral and/or organic mixtures, such as soil, with measuring accuracies which fall noticeably above the measuring accuracies of prior art methods, and which do not require sample specific calibrations to be performed in the laboratory.

This is accomplished in accordance with the method of the invention by introducing a measuring probe at a given position in the mixture without changing the density of the mixture and such that an exterior wall of the probe lies closely against the mixture. Measuring electrodes of the probe are charged with a high frequency electromagnetic wave so as to generate an HF field in a region of the electrodes and reflect a wave from the electrodes. A measurement of a complex reflection factor of the reflected wave at a temperature $T_1$ of the mixture is taken. Then the the probe and the surrounding mixture are cooled to a temperature $T_2$ such that all water in a volume of the mixture covering most of the HF field is frozen and the complex reflection factor with the surrounding mixture at the temperature $T_2$ is measured. The dielectric constant for the mixture at the temperatures $T_1$ and $T_2$ is determined from the measured complex reflection factors with the aid of an invariable probe-specific calibration curve, and the volumetric water content of the mixture is calculated from the two determined dielectric constants and the known dielectric constants of water and ice. In the preferred embodiment, the cooling of the probe and surrounding mixture is performed by liquid nitrogen so that the water in a volume covering approximately 99% of the HF field is frozen and the temperature $T_2$ of the surrounding mixture falls to within a range from $-2°$ C. to $-20°$ C.

The apparatus according to the invention includes a probe body having a hollow cylinder formed of an insulating material and formed with an annular cutting edge at a lower end, the cutting edge lying at an outer surface of the cylinder. At least one electrode arrangement is carried by the probe body. A bottom plate which may be disposed adjacent to the lower end of the cylinder is provided so that the cylinder and the bottom plate define a cavity in the cylinder above the bottom plate, the bottom plate sealing the lower end against passage therethrough of a coolant in the cavity. A temperature sensor is provided in a region of the electrode arrangement. A removable cover is provided for closing an upper end of the cavity. In the preferred embodiment, the electrode arrangement is a two or three-conductor system, the probe body is temperature resistant down to $-180$ degrees C., and the cutting edge of the probe body has cutting faces forming an angle of $10°$ to $15°$.

The error caused in prior art methods by a change of density of the soil due to the placement of the probe in the soil is reduced significantly according to the invention in that the cutting edge of the probe is pressed lightly into the soil so as to press the portion of the soil taken up by the probe body inwardly of the cylinder. The soil material is removed from the interior of the probe body with the aid of an earth auger and then the probe is pushed further into the soil. Instead of pressing the probe body into the soil in a continuous manner, one may obtain quite satisfactory results with the hammering action of a hammer drill. The repeated pressing (or hammering) of the probe into the soil and removal of soil out of the probe, until the probe is located at the desired position in the soil ensures that a practically gap-free contact is made between the probe and the soil, without changes in density of the volume of soil being measured.

The measurement error in the methods of the prior art caused by the non-consideration of B and $\epsilon_B$ is avoided by the invention in that, after a first dielectric constant measurement the water in the volume being measured is frozen and a second measurement of the dielectric constant of the mixture is made. This second measured dielectric constant $\epsilon_{g2}$ is a function of the quantity of the water now converted to ice, according to the equation:

$$\epsilon_{g2} = B \cdot \epsilon_B + W \cdot \epsilon_E + L \cdot \epsilon_L$$

where $\epsilon_E = 3.05$ is the dielectric constant of the ice.

If the probe remains at the same location, B and $\epsilon_B$ do not change. The water content changes only with a simultaneous and corresponding change of the air content. Thus, if the probe remains at the same location, and one forms the difference $\epsilon_{g1} - \epsilon_{g2}$, the terms $B \cdot \epsilon_B$ and $L \cdot \epsilon_L$ are canceled out in the above equation, so that W can be calculated as follows:

$$W = \frac{\epsilon_{g1} - \epsilon_{g2}}{\epsilon_W - \epsilon_E}$$

Thus, in contrast to the methods of the prior art, the method according to the invention does not require a determination of a mixture specific calibration curve.

After the second measurement of dielectric constant has been taken and the mixture has been permitted to thaw, if a determination of the water content of the mixture at a later time is to be made, e.g., after a change in the water content, W, caused, for example by rain, the dielectric constant $\epsilon_{g3}$ of the mixture is again measured. Since $\epsilon_{g3}$ is related to a change $\Delta W$ in the water content according to the equation $$\epsilon_{g3} = B \cdot \epsilon_B + (W + \Delta W) \cdot \epsilon_W + (L - \Delta W) \cdot \epsilon_L,$$

the change $\Delta W$ can be calculated with the following formula:

$$\Delta W = \frac{\epsilon_{g3} - \epsilon_{g1}}{\epsilon_W - \epsilon_L}$$

if the temperature of the water and thus the temperature dependent values of $\epsilon_W$ have not changed.

Since $\epsilon_W$ is a function of the water temperature, values for $\epsilon_W$ corresponding to the actual temperatures are used in the first and third measurements. In order to know these temperatures, temperature sensors are installed in the measuring probe in the vicinity of the measuring electrodes. If the temperature of the water has changed, then $\Delta W$ is calculated from the above formulas for $\epsilon_{g1}$ and $\epsilon_{g3}$.

During cooling of the mixture, $\epsilon_g$ decreases and reaches a minimum value $\epsilon_{g2}$ when a local minimum is reached in the $\epsilon_g$ temperature curve. This minimum indicates that the water in the volume of the mixture being measured is completely frozen.

BRIEF DESCRIPTION OF THE DRAWING

These and other features and advantages of the invention may be more completely understood from the following detailed description of the preferred embodiments of the invention with reference to the accompanying drawing which figure is a partially schematic block diagram and partially schematic cross-sectional illustration of an embodiment of the measuring probe according to the invention.

DESCRIPTION OF THE PREFERRED EMBODIMENTS

Referring to the figure, a probe body 1 is composed of a hollow cylinder made of a cold temperature resistant insulating material. Glass fiber reinforced polyester resin has been found to be a satisfactory material. Preferably, the probe body 1 is temperature resistant down to $-180$ degrees C.

The body 1 is provided with a cutting edge 20 at a lower end of its cylindrical outer surface. The cutting edge has cutting faces forming an angle of preferably $10°$ to $15°$. Such a cutting edge facilitates introduction of the probe body into the soil such that soil taken up by the probe body is pressed into the cylinder, thereby substantially avoiding compression of the soil to be measured.

The body 1 carries an electrode arrangement 3 which is preferably realized as a dual conductor or a triple conductor system and here forms a high frequency strip conductor. This high frequency strip conductor is applied to the outer cylindrical surface in the form of ring segments. In order that the probe may have improved temperature stability with only an insignificant reduction in its sensitivity, the electrode arrangement 3 can be embedded in the cylindrical walls of the probe body 1 or so as to be covered by a thin layer of insulating material.

An electromagnetic wave generated by a high frequency generator 9 is conducted through a bidirectional coupler 8 to the electrode arrangement 3 via a coaxial cable 6 and an impedence corrector 7. A radiation field 4 created by the wave is emitted by the electrode arrangement 3 so as to penetrate the material to be measured, e.g. a soil mixture. A portion of the wave is reflected from electrode arrangement 3, with the magnitude and phase of the reflected wave depending on the dielectric constant and the conductivity of the soil mixture. A temperature sensor 17 provided on the probe body 1 in the vicinity of the electrode arrangement 3 measures the actual temperature of the mixture.

A vector voltmeter 10 measures the magnitude and phase, i.e., the complex reflection factor, of the reflected wave, and a computer 14 calculates the dielectric constant and conductivity of the mixture from these measurements. The association of the reflected wave with the dielectric constant and the conductivity of the mixture being measured can be calculated theoretically according to particulars of the probe construction. However, in order to adapt this association more precisely to the realized probe, a single series of probe specific calibration measurements is performed. Phase and amplitude measurements are made for known mixtures. From these calibration measurements, probe or manufacturing specific input data values for the above mentioned association calculation, which are selected so that the calibration measurements coincide with the calculated results. These selected input data are stored in the computer 14 for use in its computation of the dielectric constant (or moisture) and conductivity from the measured complex reflection forces.

After setting the probe body 1 in the soil mixture to be measured, and possibly after once measuring the conductivity and dielectric constant, all as described above, a bottom plate 18 is inserted to seal the bottom of the probe body to make it possible to collect the liquid coolant, usually liquid nitrogen, in the probe cavity 2. Preferably, the extent of freezing should be sufficient to cover approximately 99% of the HF field and so as to cool the surrounding mixture to a temperature $T_2$ within a range from $-2°$ C. to $-20°$ C. After measuring the frozen soil mixture, a cover 5 is brought over the probe body 1 so that a further measurement may be made after a change in the water content of the soil mixture, e.g. after or during a rain. A channel 5' in the cover 5 conducts rain water dropping onto the cover surface far enough away that its influence on the measuring field is insignificant. In this way the water flowing away from the cover does not contribute to an enrichment of moisture in the measuring volume.

In addition to performing the multiple determinations of the dielectric constant of the mixture as described above, the computer 14 calculates the moisture content of the mixture according to the above described formula:

$$W = \frac{\epsilon_{g1} - \epsilon_{g2}}{\epsilon_W - \epsilon_E}$$

where W is the fractional amount of moisture in the mixture, $\epsilon_{g1}$ is the first measured dielectric constant of the mixture with the mixture at the temperature $T_1$, $\epsilon_{g2}$ is the measured dielectric constant of the mixture with the water frozen, $\epsilon_E = 3.05$ is the dielectric constant of the frozen water, and $\epsilon_W$ is the dielectric constant of the water during the first measurement (when the mixture is at the temperature $T_1$).

The determination of change in moisture content can be calculated by the computer 14 according to the above described formula $$\Delta W = \frac{\epsilon_{g3} - \epsilon_{g1}}{\epsilon_W - \epsilon_L}$$

if the temperature of the water has not changed, where $\Delta W$ is the fractional increase in the moisture content of the mixture, $\epsilon_{g3}$ is the measured dielectric constant of the mixture after the change in moisture content, and $\epsilon_L$ is the dielectric constant of air. If the water temperature has changed, the above formulae for $\epsilon_{g1}$ and $\epsilon_{g3}$ are used. The results of the moisture calculations and the determination of conductivity are respectively output by the computer 14 on a moisture data output line 15 and a conductivity data output line 16 which may be connected to a data collection system.

The high frequency waves are conducted through the high frequency cables 6. If the frequency of generator 9 is selected high enough that the electronic quality factor Q of the mixture being measured becomes greater than 3, then the conductivity influences the phase of the reflected wave only to a negligible degree. Here the quality factor Q is defined by:

$$Q = \frac{\epsilon_g \cdot \omega}{\delta}$$

where $\omega$ = the oscillation frequency of the generator, and
$\delta$ = conductivity of the mixture being measured.

If the phase of the reflected wave is substantially independent of the conductivity of the mixture, then a single calibration curve is sufficient between phase and dielectric constant in order to replace the above-described general association. In this case, a conventional electronic memory circuit 11 can store the calibration curve and drive the dielectric constant display 12 and a conductivity display 13 for monitoring the condition Q>3 at its outputs. The moisture content of the mixture, of course, can be readily determined from the dielectric constant values as described above.

The calibration curve between phase and dielectric constant is generally not linear. With increasing dielectric constant, the phase increases by an increasingly slower rate. However, if the length of the electrode arrangement 3 is selected to be somewhat shorter than ¼ of the wavelength of the HF wave from the generator 9 at the maximum dielectric constant is to be expected, a substantial linearization of the calibration curve is realized. The increase in resonance of the $\lambda/4$ line resonator formed by the electrode arrangement sufficiently compensates the non-linearity.

It will be understood that the above description of the present invention is susceptible to various modifications, changes and adaptations, and the same are intended to be comprehended within the meaning and range of equivalents of the appended claims.

What is claimed is:

1. A method of determining the volumetric water content of a mineral and/or organic mixture having a density, comprising the steps of:
(a) introducing a measuring probe having measuring electrodes and an exterior wall at a given position in the mixture without changing the density of the mixture and such that the exterior wall of the probe lies closely against the mixture;
(b) charging the measuring electrodes with a high frequency electromagnetic wave so as to generate an HF field in a region of the measuring electrodes, and to reflect a wave from the electrodes,
(c) measuring a complex reflection factor of the reflected wave at a temperature $T_1$ of the mixture;
(d) cooling the probe and the surrounding mixture to a temperature $T_2$ such that all water in a volume of the mixture covering most of the HF field is frozen;
(e) measuring the complex reflection factor of the reflected wave with the surrounding mixture at the temperature $T_2$;
(f) determining the respective dielectric constants for the mixture at the temperatures $T_1$ and $T_2$ from the complex reflection factors measured in said steps (c) and (e), with the aid of an invariable probe-specific calibration curve; and
(g) calculating the volumetric water content of the mixture from the two dielectric constants of the mixture determined in said step (f) and known dielectric constants of water and ice.

2. A method as defined in claim 1, wherein said step (d) includes cooling the probe and surrounding mixture with liquid nitrogen.

3. A method as defined in claim 1, wherein said step (d) includes freezing the water in a volume covering approximately 99% of the HF field.

4. A method as defined in claim 1, wherein said step (d) includes cooling the surrounding mixture to the temperature $T_2$ within a range from $-2°$ C. to $-20°$ C.

5. A method as defined in claim 1, further comprising the step of determining a change in volumetric water content, including
(h1) taking only one further measurement of the complex reflection factor at the actual temperature of the mixture and with the measuring probe at the given position,
(h2) determining the dielectric constant of the mixture from the one further measurement, and
(h3) determining the change in water content from the dielectric constant determined in said step (h2), the dielectric constant determined in said step (f), the known dielectric constant of the water and the known dielectric constant of air.

6. A method as defined in claim 1, wherein said step of charging the measuring electrodes with a high frequency electromagnetic wave comprises the step of charging the measuring electrodes with an electromagnetic wave having a frequency which is sufficiently high that the electrical quality factor Q of the mixture is greater than 3, and said step (f) comprises the step of determining the dielectric constant for the mixture at the temperatures $T_1$ and $T_2$ from phase components alone of the complex reflection factors measured in said steps (c) and (e), with the aid of an invariable probe-specific calibration curve.

7. A method as defined in claim 1, wherein the mineral and/or organic mixture comprises a soil.

8. A method as defined in claim 1, further comprising the steps of measuring the temperatures $T_1$ and $T_2$.

9. An apparatus for determining the volumetric water content of a mineral and/or organic mixture, the apparatus comprising:
a probe body including a hollow cylinder formed of an insulating material and having an annular cutting edge at a lower end, the cutting edge lying at an outer surface of the cylinder;
at least one electrode arrangement carried by the probe body;
a bottom plate removably disposed adjacent to said lower end of the cylinder so that said cylinder and said bottom plate define a cavity in the cylinder above the bottom plate, the bottom plate sealing the lower end against passage therethrough of a coolant in the cavity;
a temperature sensor in a region of the at least one electrode arrangement; and
a cover removably disposable over the cavity for closing an upper end of the cavity.

10. An apparatus as defined in claim 9 wherein the cylinder is temperature resistant down to $-180°0$ C.

11. An apparatus as defined in claim 9 wherein the cutting edge has cutting faces forming an angle of $10°$ to $15°$.

12. An apparatus as defined in claim 9, wherein the electrode arrangement includes two measuring electrodes.

13. An apparatus as defined in claim 12, wherein the measuring electrodes lie directly on the exterior surface of the probe body.

14. An apparatus as defined in claim 12, further comprising a thin insulating layer on the measuring electrodes for separating the measuring electrodes from the mixture.

15. An apparatus as defined in claim 12, further comprising means for applying an electromagnetic wave of a given wavelength to the measuring electrodes, wherein the measuring electrode arrangement has a length which is close to $\frac{1}{4}$ of the given wavelength.

16. An apparatus as defined in claim 9, wherein the cover is seated tightly on and flush with the probe body, the cover having a discharge channel for carrying rain water away from the cylinder.

17. A method of determining the volumetric water content of a mineral and/or organic mixture, comprising the steps of:
providing an apparatus, the apparatus including
a probe body including a hollow cylinder formed of an insulating material and having an annular cutting edge at a lower end, the cutting edge lying at an outer surface of the cylinder,
at least one electrode arrangement carried by the probe body,
a bottom plate removably disposed adjacent to said lower end of the cylinder so that said cylinder and said bottom plate define a cavity in the cylinder above the bottom plate, the bottom plate sealing the lower end against passage therethrough of a coolant in the cavity,
a temperature sensor in a region of the at least one electrode arrangement, and
a cover removably disposable over the cavity for closing an upper end of the cavity; and
using the apparatus for a determination of the volumetric water content of a soil.

* * * * *